(12) United States Patent
Braley et al.

(10) Patent No.: US 10,172,920 B2
(45) Date of Patent: Jan. 8, 2019

(54) SLEEP APNEA TREATMENT

(71) Applicant: The Regents of The University of Michigan, Ann Arbor, MI (US)

(72) Inventors: Tiffany J. Braley, Ypsilanti, MI (US); Benjamin Segal, Ann Arbor, MI (US); Ronald D. Chervin, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 449 days.

(21) Appl. No.: 14/407,786

(22) PCT Filed: Jun. 14, 2013

(86) PCT No.: PCT/US2013/045954
§ 371 (c)(1),
(2) Date: Dec. 12, 2014

(87) PCT Pub. No.: WO2013/188806
PCT Pub. Date: Dec. 19, 2013

(65) Prior Publication Data
US 2015/0139935 A1 May 21, 2015

Related U.S. Application Data

(60) Provisional application No. 61/659,737, filed on Jun. 14, 2012.

(51) Int. Cl.
| | | |
|---|---|---|
| *A61K 31/194* | (2006.01) | |
| *A61K 31/225* | (2006.01) | |
| *A61K 38/07* | (2006.01) | |
| *A61K 38/16* | (2006.01) | |
| *A61K 38/21* | (2006.01) | |

(52) U.S. Cl.
CPC .......... *A61K 38/215* (2013.01); *A61K 31/194* (2013.01); *A61K 31/225* (2013.01); *A61K 38/07* (2013.01); *A61K 38/16* (2013.01)

(58) Field of Classification Search
None
See application file for complete search history.

(56) References Cited

U.S. PATENT DOCUMENTS

| | | |
|---|---|---|
| 2002/0165246 A1 | 11/2002 | Holman |
| 2004/0142956 A1 | 7/2004 | Chen et al. |
| 2005/0222209 A1* | 10/2005 | Zeldis .................. A61K 31/445 514/323 |
| 2005/0239838 A1* | 10/2005 | Edgar .................. A61K 31/445 514/319 |
| 2008/0089861 A1 | 4/2008 | Du et al. |
| 2010/0256229 A1 | 10/2010 | Shoucheng et al. |

FOREIGN PATENT DOCUMENTS

| | | |
|---|---|---|
| WO | 99/25356 | 5/1999 |
| WO | 2007016203 A1 | 2/2007 |
| WO | 2007051259 A1 | 5/2007 |

OTHER PUBLICATIONS

Ma (Modern Drug Discovery 2004, 7(6)).*
Waiker et al (J Am Soc Nephrol. Jan. 2012; 23(1): 13-21).*
Hudgel (Am J Respir Crit Care Med vol. 158. pp. 691-699, 1998).*
Veasey et al (Sleep, vol. 29, No. 8, 2006).*
Epstein et al (J Clin Sleep Med. Jun. 15, 2009;5(3):263-76).*
Alberti et al., "Plasma cytokine levels in patients with obstructive sleep apnea syndrome: a preliminary study." J Sleep Res. Dec. 2003; 12(4):305-11.
Altmeyer et al., "Antipsoriatic effect of fumaric acid derivatives. Results of a multicenter double-blind study in 100 patients." J Am Acad Dermatol. Jun. 1994; 30(6):977-81.
American Academy of Sleep Medicine Task Force. (1999). Sleep-related breathing disorders in adults: recommendations for syndrome definition and measurement techniques in clinical research. Sleep 1999, 22(5):667-689.
Brousil et al., "Cladribine: an investigational immunomodulatory agent for multiple sclerosis." Ann Pharmacother. Oct. 2006; 40(10):1814-21.
Brunmark et al., "The new orally active immunoregulator laquinimod (ABR-215062) effectively inhibits development and relapses of experimental autoimmune encephalomyelitis." J Neuroimmunol. Sep. 2002; 130(1-2): 163-72.
Buyssee et al., "The Pittsburgh Sleep Quality Index: a new instrument for psychiatric practice and research." Psychiatry Res. May 1989; 28(2):193-213.
Carson et al., "Specific toxicity of 2-chlorodeoxyadenosine toward resting and proliferating human lymphocytes." Blood. Oct. 1983; 62(4):737-43.
Chervin et al., "Sleep onset REM periods during multiple sleep latency tests in patients evaluated for sleep apnea." Am J Respir Crit Care Med. Feb. 2000; 161(2 Pt 1):426-31.
Cohen et al., "Oral Fingolimod or Intramuscular Interferon for Relapsing Multiple Sclerosis." New England Journal of Medicine, 362(5):402-415
Confavreux et al., "Safety of teriflunomide in the treatment of relapsing multiple sclerosis: results over an 8-year extension." Mult Scler 2010, 16: S291.
Dhib-Jalbut, "Mechanisms of interferon beta action in multiple sclerosis." Mult Scler. Dec. 1997; 3(6):397-401.
Iber, The AASM manual for the scoring of sleep and associated events: rules, terminology and technical specifications. American Academy of Sleep Medicine. 2007.
Johns, "A new method for measuring daytime sleepiness: the Epworth sleepiness scale." Sleep. Dec. 1991; 14(6):540-5.

(Continued)

*Primary Examiner* — Brian Gangle
*Assistant Examiner* — Andrea K McCollum
(74) *Attorney, Agent, or Firm* — Casimir Jones S.C.; David Casimir; Thomas Isenbarger

(57) ABSTRACT

Provided herein is technology relating to treating sleep apnea and particularly, but not exclusively, to treating sleep apnea with immunotherapeutics and/or anti-inflammatory drugs such as beta-interferons and glatiramer acetate.

15 Claims, 1 Drawing Sheet

(56) References Cited

OTHER PUBLICATIONS

Kappos et al. "Oral fumarate (BG00012) for relapsing-remitting multiple sclerosis: results of a phase 2b study." Lancet 372 (2008): 1463-1472.
Kolbach et al., "Fumaric acid therapy in psoriasis: Results and side effects of 2 years of treatment" J Am Acad Dermatol. Nov. 1992; 27(5 Pt 1):769-71.
Li et al., "Long-term brain MRI and clinical assessments of teriflunomide for the treatment of multiple sclerosis: extension of a Phase II study" Mult Scler 2010, 16: S142.
Lin et al. "The anti-inflammatory effects of dimethyl fumarate in astrocytes involve glutathione and haem oxygenase-1." ASN Neuro. Apr. 7, 2011;3(2) e00055.
Moharregh-Khiabani et al., "Fumaric Acid and its esters: an emerging treatment for multiple sclerosis." Curr Neuropharmacol. Mar. 2009; 7(1):60-4.
Montalban et al., "Oral cladribine added to interferon beta-1a for active multiple sclerosis: a 96-week, double-blind, placebo-controlled phase IIb study." Multiple Sclerosis 2007, 13:S245-S246.
Mrowietz et al., "Treatment of psoriasis with fumaric acid esters: results of a prospective multicentre study. German Multicentre Study." Br J Dermatol. Mar. 1998; 138(3):456-60.
Murdoch et al., "Spotlight on subcutaneous recombinant interferon-beta-1a (Rebif) in relapsing-remitting multiple sclerosis." BioDrugs. 2005; 19(5):323-5.
O'Connor et al., "A placebo-controlled phase III trial (TEMSO) of oral teriflunomide in relapsing multiple sclerosis: clinical efficacy and safety outcomes" Mult Scler 2010, 16(10 Suppl):S23.
Rechtshaffen "A manual of standardized terminology, techniques and scoring system for sleep stages of human subjects." 1968.
Remington's Pharmaceutical Sciences, Mack Publishing Co. 1985 ed.
Rieckmann et al., "Cladribine tablets in relapsing-remitting multiple sclerosis: study design of the 2-year, Phase ILLb CLARITY (CLAdRibine tablets Treating multiple sclerosis orallY) extension study." Multiple Sclerosis 2008, 14:S161-S162.
Sawhney et al., "Bioerodible hydrogels based on photopolymerized poly(ethylene glycol)-co-poly(.alpha.-hydroxy acid) diacrylate macromers" Macromolecules 1993, 26(4):581-587.
Schimrigk, S., et al. "Oral fumaric acid esters for the treatment of active multiple sclerosis: an open-label, baseline-controlled pilot study." European journal of neurology 13.6 (2006): 604-610.
Shahar et al., "Sleep-disordered breathing and cardiovascular disease: cross-sectional results of the Sleep Heart Health Study." Am J Respir Crit Care Med. Jan. 2001; 163(1):19-25.
Vgontzas et al., "Marked decrease in sleepiness in patients with sleep apnea by etanercept, a tumor necrosis factor-alpha antagonist." J Clin Endocrinol Metab. Sep. 2004; 89(9):4409-13.
Webster et al., "The Functional Assessment of Chronic Illness Therapy (FACIT) Measurement System: properties, applications, and interpretation." Health Qual Life Outcomes. Dec. 16, 2003; 1:79.
White, "Central sleep apnea." Med Clin North Am. Nov. 1985; 69(6):1205-19.
Wolinsky et al., "A placebo-controlled phase III trial (TEMSO) of oral teriflunomide in relapsing multiple sclerosis: magnetic resonance imaging (MRI) outcomes." Mult Scler 2010, 16: S347.
Kheirandish et al., "Intranasal Steroids and Oral Leukotriene Modifier Therapy in Residual Sleep-Disordered Breathing After Tonsillectomy and Adenoidectomy in Children" Pediatrics 2006;117;e61.
Federal Drug Administration, Full Prescribing Information for Copaxone; Feb. 2009.

\* cited by examiner

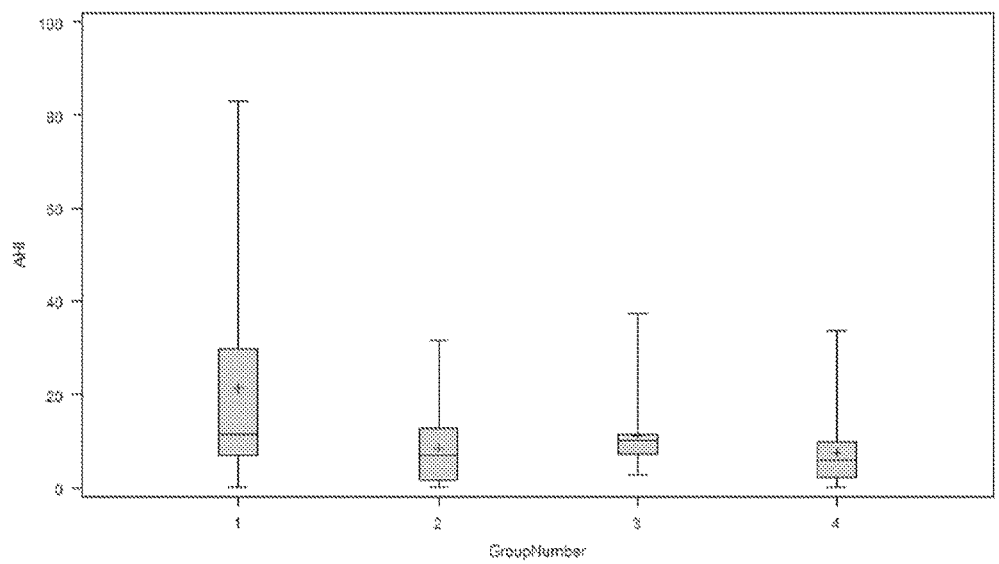
A
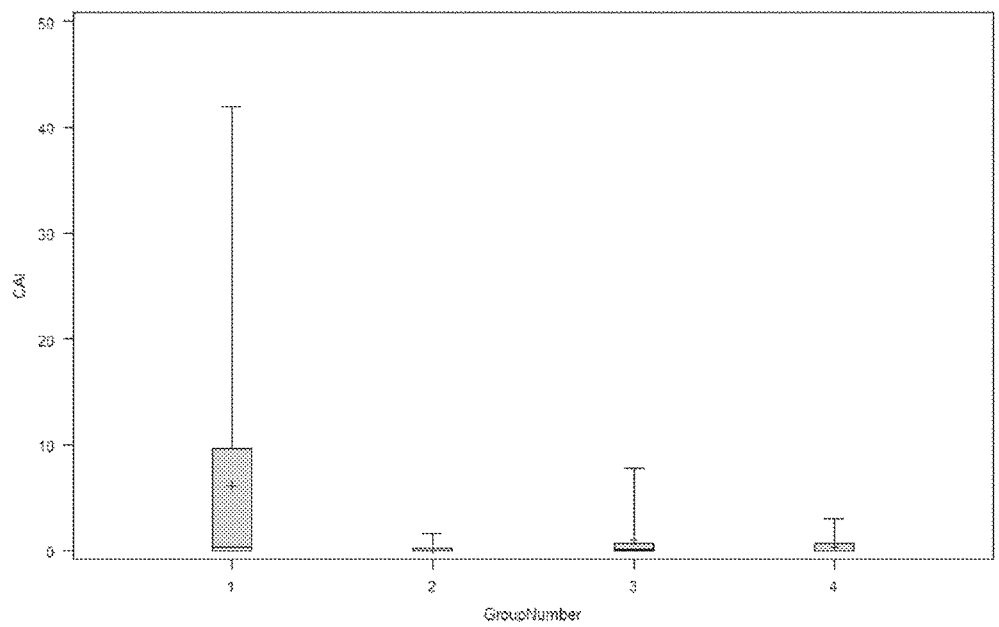
B

SLEEP APNEA TREATMENT

This application is a national phase application under 35 U.S.C. § 371 of PCT International Application No. PCT/US2013/045954, filed Jun. 14, 2013, which claims priority to U.S. Provisional Patent Application No. 61/659,737, filed Jun. 14, 2012, each of which is herein incorporated by reference in its entirety.

FIELD OF INVENTION

Provided herein is technology relating to treating sleep apnea and particularly, but not exclusively, to treating sleep apnea with immunotherapeutic drugs such as beta-interferons and glatiramer acetate.

BACKGROUND

Obstructive sleep apnea (OSA) is a common medical condition that is characterized by repeated upper airway obstruction during sleep, despite efforts to breathe. Upper airway patency, normally maintained by afferent sensory input to cranial nuclei and efferent output to the upper airway, is altered in OSA. Patients often stop breathing hundreds of times during the night, limiting the amount of oxygen delivered to the brain and rest of the body. These pauses in breathing may eventually increase risk for stroke, myocardial infarction, arrhythmia, heart failure, and premature death. According to the National Heart, Lung, and Blood Institute, at least 1 in 10 people over the age of 65 suffer from sleep apnea. Other statistical measures demonstrate that approximately 2-4% of the adult population of the United States suffer from sleep apnea. Productivity losses associated with daytime sleepiness are significant and, as such, the economic burdens associated with sleep apnea are steadily increasing, thus making OSA a major public health concern.

In addition to obstructive sleep apnea (OSA), central sleep apnea (CSA) is another common form of sleep-disordered breathing. Central sleep apnea results from recurrent complete or partial absence of respiratory effort and can be caused by impaired respiratory control at the level of the medullary reticular formation. Although in the general population the prevalence of CSA is lower than that of OSA, patients with disorders such as MS that affect the brainstem may be at increased risk for CSA or apnea-related sudden death. Cases of both obstructive and central sleep apnea in structural and ischemic brainstem syndromes are well documented.

Accordingly, diagnosing and treating sleep apnea is important because of its strong association with and potential cause of several serious medical conditions, such as hypertension, cardiovascular disease, coronary artery disease, insulin-resistance diabetes, depression, and sleepiness-related accidents. Sleep apnea is a treatable risk factor for cardiovascular disease, motor vehicle accidents, fatigue, and decreased quality of life.

Current treatments for sleep apnea are cumbersome and physically intrusive, such as administering continuous positive airway pressure (CPAP), which involves wearing a mask every night to splint the upper airway open during sleep. Some patients have surgery to treat their obstructive sleep apnea, and others use an oral appliance nightly.

Currently, there are no effective pharmacologic treatments for obstructive sleep apnea. Consequently, drugs for treating sleep apnea will be life-altering to many throughout the world.

SUMMARY

Accordingly, provided herein is technology related to pharmacotherapies for treating sleep apnea, for example immunotherapeutic agents. In some embodiments, drugs used to treat multiple sclerosis (MS) are used. These drugs include a class of medications known as the beta-interferons (e.g., interferon beta-1a and interferon beta-1b) and another treatment called glatiramer acetate (e.g., marketed in some formulations as COPAXONE glatiramer acetate). Other immunotherapeutics, some of which are administered orally, some of which are administered intravenously, and some of which are administered by subcutaneous or intramuscular injection, are also encompassed within the scope of the technology. In some modes of action, these medications work by modulating the immune system to reduce inflammatory processes.

Accordingly, provided herein is technology related in some aspects to methods of treating a subject in need of a treatment for sleep apnea, for example, a method comprising administering an immunotherapy to a subject in need of a treatment for sleep apnea. In some embodiments, the immunotherapy is an anti-inflammatory drug and in some embodiments, the immunotherapy does not have immunosuppressant activity. Many types of immunotherapeutics are contemplated as pharmacologic agents to treat sleep apnea. For example, in some embodiments the immunotherapeutic agent is a beta-interferon, in some embodiments the immunotherapeutic agent is glatiramer acetate, and in some embodiments the immunotherapeutic agent is BG00012 (e.g., dimethyl fumarate sold under the trade name TECFIDERA). In specific embodiments of the technology, the beta-interferon is selected from the group consisting of interferon beta-1a and interferon beta-1b. In some embodiments, the immunotherapeutic agent is Fingolimod (e.g., sold under the trade name GILENYA) and in some embodiments the immunotherapeutic is Teriflunomide (e.g., sold under the trade name AUBAGIO).

The technology is not limited in the form of sleep apnea that is treated according to the methods provided herein. For example, in some embodiments, the sleep apnea is obstructive sleep apnea and in some embodiments the sleep apnea is a central sleep apnea.

During the development of embodiments of the technology, data demonstrated that MS patients treated with immunotherapeutic agents had reduced sleep apnea. Accordingly, in some embodiments the methods comprise treating a subject who has MS or is suspected of having MS. However, many subjects suffering from sleep apnea do not also have MS; thus, in some embodiments, the subject does not have MS or is not suspected to have MS.

Certain quantitative measures are used to assess the severity of a subject's sleep apnea. For example, in some embodiments the technology comprises a method wherein the subject has an apnea-hypopnea index (AHI) of at least 5 apnea episodes per hour of sleep, a significant component of central sleep apnea defined by a central sleep apnea index of at least 5 episodes per hour of sleep (e.g., in the absence of severe obstructive sleep apnea), and/or a central apnea index (CAI) that is at least 15 apnea episodes per hour of sleep in the presence of severe concomitant obstructive sleep apnea (apnea-hypopnea index greater than or equal to 30 episodes per hour of sleep). In some embodiments, the AHI and/or CAI are measured by polysomnography.

In some embodiments, the subject has a regional brainstem dysfunction. Additionally, in some embodiments the subject has impaired respiratory control at the level of the medullary reticular formation; dysarthria or dysphagia; lower cranial nerve dysfunction; and/or midbrain, pontine, or medullary lesions.

In some embodiments, the subject is a child (e.g., an infant, a prepubertal child) and the sleep apnea is a pediatric sleep apnea.

The immunotherapeutic agent is used in some embodiments to provide a pharmaceutical formulation. Thus, in some embodiments, the technology relates to methods wherein a pharmaceutical formulation comprises the immunotherapy. In some embodiments, the pharmaceutical formulation is administered orally and in some embodiments the pharmaceutical formulation is administered by injection, e.g., subcutaneously, intramuscularly, etc.

In some embodiments, patients are tested, e.g., to select subjects for treatment, to follow the course of treatment, to assess the effectiveness of treatment, to modify the treatment, etc. For example, in some embodiments, methods are provided further comprising testing the subject for sleep apnea. In some embodiments, the testing occurs before the administering. In some embodiments, the administering occurs before the testing. Additionally, some embodiments further comprise a second testing after the administering, and some embodiments further comprise a second administering after the testing. Embodiments are also within the scope of the technology comprising testing and administering in various other combinations and cycles of repetition.

In some embodiments, testing produces a quantitative measure of sleep apnea. Accordingly, in some embodiments, the testing produces a quantitative sleep apnea score and the second testing produces a second quantitative sleep apnea score and a relative change in the second quantitative sleep apnea score compared to the quantitative sleep apnea score indicates an amelioration of sleep apnea in the patient. Testing, in some embodiments, is used to modify the second administering relative to a previous administering. Among the various measures of sleep apnea, in some embodiments the quantitative sleep apnea score is AHI and/or CAI as determined by polysomnography.

In some embodiments, administering an immunotherapy to a patient in need of a treatment for sleep apnea reduces or eliminates one or more signs or symptoms of sleep apnea; prevents increased severity of one or more signs or symptoms of sleep apnea; or reduces, prevents, or eliminates an associated disease or condition. For instance, in some embodiments, the administering improves sleep quality and/or sleep quantity of the subject, e.g., as determined by measuring a Pittsburgh Sleep Quality Index score, an Epworth Sleepiness Scale score, or a Functional Assessment of Chronic Illness Therapy-Fatigue Scale score. See, e.g., Buysse, et al. (1989). "The Pittsburgh Sleep Quality Index (PSQI): A new instrument for psychiatric research and practice", *Psychiatry Research,* 28: 193-213; Johns (1991). "A new method for measuring daytime sleepiness: the Epworth sleepiness scale", *Sleep* 14: 540-5; Webster, et al. (2003), "The Functional Assessment of Chronic Illness Therapy (FACIT) Measurement System: properties, applications, and interpretation", *Health and Quality of Life Outcomes* 1:79, each incorporated herein by reference.

In some embodiments, the administering reduces or eliminates systemic or localized inflammation. In some embodiments, the administering prevents systemic or localized inflammation. Embodiments of the technology provide that administering an immunotherapy to a subject in need of a treatment for sleep apnea prevents sleep apnea. In addition, in some embodiments, the administering reduces or prevents an increase in a level of an inflammatory cytokine and in some embodiments, the administering reduces or prevents an increase in a level of TNF-alpha or a level of interleukin-6.

The methods are not limited in the types or categories of subjects that are administered an immunotherapy. For example, in some embodiments the subject has sleep apnea or is at risk of developing sleep apnea. In some embodiments, the subject is not in need of a treatment for MS and in some embodiments the subject has not been treated for MS.

Combination therapies are an aspect of the technology; for instance, in some embodiments, the technology comprises co-administering an additional therapeutic agent or medical intervention, e.g., in some embodiments the medical intervention is CPAP; in some embodiments, the medical intervention is surgery; and, in some embodiments, the medical intervention is weight loss. In some embodiments, the immunotherapy and the additional therapeutic agent are administered simultaneously and in some embodiments the immunotherapy and the additional therapeutic agent are administered sequentially.

The technology comprises in one aspect the use of an immunotherapeutic agent for the manufacture of a medicament for treating a subject having sleep apnea. In addition, the technology provides, in some embodiments, an immunotherapy for the treatment of sleep apnea and, in some embodiments, an immunotherapy for use in treating sleep apnea.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1 shows boxplots of the apnea/hypopnea index (AHI) and the central apnea index (CAI) for MS patients, stratified by the presence or absence of brainstem involvement, and their respective matched controls. FIG. 1A (Top): AHI for n=20 MS patients with brainstem involvement versus 40 matched controls (groups 1 and 2), and n=16 MS patients without brainstem involvement versus 32 matched controls (groups 3 and 4); FIG. 1B (Bottom): CAI for n=20 MS patients with brainstem involvement versus 40 matched controls (groups 1 and 2), and n=16 MS patients without brainstem involvement vs. 32 matched controls (groups 3 and 4).

The figures are depictions that are intended to bring clarity and understanding to various embodiments of the technologies disclosed herein. Moreover, it should be appreciated that the drawings are not intended to limit the scope of the present teachings in any way.

DETAILED DESCRIPTION

Provided herein is technology relating to treating sleep apnea and particularly, but not exclusively, to treating sleep apnea with immunotherapeutic agents and/or anti-inflammatory drugs such as beta-interferons and glatiramer acetate. Data collected demonstrate that MS-associated clinical features increase sleep apnea risk when controlling for other MS-unrelated clinical features known to influence this risk. Analysis of the data demonstrated that use of disease modifying therapy (e.g., immunotherapeutics such as beta-interferon and/or glatiramer acetate) emerged as a predictor of diminished apnea severity. In particular, disease modifying therapy use eclipsed the individual effects of other modeled variables known to influence quantitative indices of sleep apnea severity.

The description of the technology uses certain section headings below. The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "subject" and "patient" refer to any animal, such as a mammal like a dog, cat, bird, livestock, and preferably a human (e.g., a human, e.g., who has sleep apnea).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (e.g., minimize or lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive versus conventional treatment).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

As used herein, the term "immunotherapy" refers to, but is not limited to, immunotherapeutic agents (e.g., pharmaceutical formulations, nutraceutical formulations, drugs, medicines, medicaments, etc.). In addition, in some contexts, "immunotherapy" is intended to include, but not limited to, agents that have immunomodulatory activity and/or immunosuppressive activity. As such, some immunotherapies are not immunomodulatory agents and some immunotherapies are not immunosuppressive agents.

Embodiments of the Technology

During the development of the technology provided herein, a cross-sectional study was conducted to assess the prevalence and severity of sleep apnea in MS patients referred for overnight polysomnography (PSG) and to explore radiographic and clinical features that might signal risk for undiagnosed sleep apnea. Apnea-hypopnea and central apnea indices (AHI and CAI, respectively) from laboratory-based PSG among 48 MS patients were compared to those of: Group A, 84 sleep-laboratory-referred, non-MS patients matched for age, gender, and body mass index; and Group B, a separate group of 48 randomly selected, referred patients. The data suggest a predisposition for obstructive sleep apnea and accompanying central apneas among MS patients, particularly among those with brainstem involvement.

Furthermore, data collected during the development of the present technology showed that MS patients who were taking particular drug therapies for their MS had significantly lower sleep apnea severity than those who were not. These drugs include a class of immunotherapeutic medications that modulate the immune system to reduce inflammatory processes (e.g., beta-interferons such as interferon beta-1a and interferon beta-1b; and glatiramer acetate). As such, provided herein is technology related to using particular MS immunotherapies (e.g., immunotherapeutic agents, e.g., drugs) to treat sleep apnea in individuals who have MS and in individuals who do not have MS.

In addition, the data collected support a causative association between inflammation and sleep apnea. For example, inflammatory cytokines TNF-alpha (tumor necrosis factor-alpha) and IL-6 (interleukin-6) are expressed at higher levels in individuals with OSA (see, e.g., Alberti A, et al. "Plasma cytokine levels in patients with obstructive sleep apnea syndrome: a preliminary study", *J Sleep Res* 2003: 12(4); 305-11), and treatment with agents that influence these cytokine levels may improve apnea severity (see, e.g., Vgontzas A N, et al. "Marked decrease in sleepiness in patients with sleep apnea by etanercept, a tumor necrosis factor-alpha antagonist", *J Clin Endocrinol Metab* 2004: 89(9); 4409-13). In contrast to previous studies (such as those referenced above) suggesting that sleep apnea may precede and cause inflammation, the data collected during the development of embodiments of the technology identify local or systemic inflammation as a contributing causative (e.g., precedent) agent to sleep apnea.

The robust differences between MS subjects and controls indicate that MS, and particularly MS-related brainstem pathology, increases vulnerability to sleep apnea. Importantly, this vulnerability is influenced by use of disease modifying therapy such as administration of immunotherapeutic agents, for example, immunomodulatory and/or anti-inflammatory drugs such as, e.g., beta-interferons and glatiramer acetate.

Accordingly, the technology provided relates to treating sleep apnea using certain immunotherapeutic (e.g., immunomodulatory and/or anti-inflammatory) drugs such as those that find use to treat MS. Although the disclosure herein refers to certain illustrated embodiments, it is to be understood that these embodiments are presented by way of example and not by way of limitation.

1. Drugs for Treating Sleep Apnea

In some embodiments, the technology relates to treating sleep apnea with an immunotherapy, e.g., an immunotherapeutic (e.g., an immunomodulatory and/or an anti-inflammatory) agent. In some embodiments, the drug is an interferon such as a beta-interferon, of which interferon beta-1a and interferon beta-1b are two particular examples. In some embodiments, the drug is glatiramer acetate; and, in some embodiments, the drug is BG00012.

1.1. Beta-Interferons

Beta-interferons (also known as IFN-β) are natural proteins produced by many mammalian cell types including lymphocytes (NK cells, B-cells, and T-cells), macrophages, fibroblasts, endothelial cells, osteoblasts, and others. Among these cell types, they are produced in large amounts by fibroblasts. Beta-interferons play a role in the innate immune response in which they stimulate both macrophages and natural killer (NK) cells to elicit anti-viral responses, e.g., to prevent the infection and propagation of viruses in an organism. Accordingly, interferon-betas are members of a class of immunotherapeutics often called "immunomodulators". Interferon beta-1a (also known as interferon beta-1-alpha) is a member of the interferon family that is produced naturally by mammalian cells. Another beta-interferon variant called interferon beta-1b is produced recombinantly in the bacterium *Escherichia coli*.

Interferons reduce the rate of MS relapses and slow the progression of disability in MS patients. While the mechanism of MS response to beta-interferons is not known, it is believed that drugs based on interferon-beta achieve their beneficial effect on MS progression as a result of their anti-inflammatory properties. However, it is not required to understand the mode of operation of beta-interferons in MS treatment to practice the technology provided herein. In a typical MS treatment, interferon beta-1a is provided as a solution for subcutaneous injection and is usually injected three times a week, or, in some treatments, injected intramuscularly once a week. Interferon beta-1b injections are administered subcutaneously and typically administered at least 48 hours apart.

Commercial forms of beta-interferon drugs include AVONEX beta-interferon, REBIF beta-interferon, CINNOVEX beta-interferon, BETASERON beta-interferon (also known as BETAFERON beta-interferon), and EXTAVIA beta-interferon.

AVONEX beta-interferon (Biogen-Idec) is the leading MS therapy in the United States and in Europe. AVONEX beta-interferon is available in two formulations, a lyophilized powder requiring reconstitution and a pre-mixed liquid syringe kit; both forms are administered once per week via intramuscular injection.

REBIF beta-interferon (Merck-Serono and Pfizer) is similar to the interferon beta protein produced by the human body and is a disease-modifying drug used to treat MS in cases of clinically isolated syndrome as well as relapsing forms of multiple sclerosis. REBIF beta-interferon is administered via subcutaneous injection three times per week and can be stored at room temperature for up to 30 days. See, e.g., Murdoch, D. 2005, "Spotlight on subcutaneous recombinant interferon-beta-1a (Rebif) in relapsing-remitting multiple sclerosis", *BioDrugs* 19(5): 323-5.

CINNOVEX beta-interferon (CinnoGen) is a recombinant interferon beta 1-a. It is produced in a lyophilized form and sold with distilled water for injection; another water-soluble variant is currently being investigated by the Vakzine Projekt Management (VPM) GmbH in Braunschweig, Germany.

BETASERON beta-interferon (Bayer), EXTAVIA beta-interferon (Novartis), and ZIFERON beta-interferon (Zistdaru Danesh Ltd.) are interferon-1b drugs used to treat relapsing forms of MS and clinically isolated syndrome. These drugs are administered by subcutaneous injection and have been shown to slow the advance of the affliction as well as reduce the frequency of attacks.

1.2. Glatiramer Acetate

Glatiramer acetate (Copolymer 1, Cop-1, or COPAXONE glatiramer acetate as marketed by Teva Pharmaceuticals) is a drug used to treat MS. It is a random polypeptide of glutamic acid, lysine, alanine, and tyrosine and has an average molecular mass of approximately 6.4 kDa. The mechanism of action for glatiramer is unknown, though knowledge of such a mechanism is not required to practice the technology. Studies in animal models of MS suggest that it has activity as an immunomodulator, in particular activating suppressor T-cells. See, e.g., Federal Drug Administration, "FULL PRESCRIBING INFORMATION [for] COPAXONE (glatiramer acetate)".

Additionally, data have shown that glatiramer acetate shifts the population of T cells from pro-inflammatory Th1 cells to regulatory Th2 cells, thus resulting in a suppression of the inflammatory response. Although the clinical definition of MS requires two or more episodes of symptoms and signs, glatiramer acetate is approved for treatment after a single episode (e.g., clinically isolated syndrome). It is also used to treat relapsing-remitting multiple sclerosis. It is administered by subcutaneous injection.

1.3. Fumaric Acid

In some embodiments, sleep apnea is treated with fumaric acid or a salt or modification thereof. Esters of fumaric acid have been used to treat psoriasis since at least 1959 (see e.g., Schweckendiek W. 1959 "Treatment of psoriasis vulgaris", *Med. Monatsschr.* 13:103-104). Subsequently, compositions comprising dimethylfumarate (DMF) and salts of ethylhydrogenfumarate (EHF) were developed as an oral psoriasis therapy and sold under the name "FUMADERM". Recently, clinical trials have demonstrated that fumaric acid, e.g., in the form of fumaric acid esters (FAE), is effective and safe as an oral immunotherapeutic agent to treat psoriasis. See, e.g., Altmeyer P J, et al. 1994, "Antipsoriatic effect of fumaric acid derivatives. Results of a multicenter double-blind study in 100 patients." *J. Am. Acad. Dermatol.* 30: 977-981; Kolbach D N et al. 1992, "Fumaric acid therapy in psoriasis: results and side effects of 2 years of treatment" *J. Am. Acad. Dermatol.* 27:769-771; Mrowietz U, et al. 1998 "Treatment of psoriasis with fumaric acid esters: results of a prospective multicentre study. German Multicentre Study", *Br. J. Dermatol.* 138: 456-460.

After ingestion, DMF, the main component of FAE (e.g., FUMADERM), is converted by esterases to the metabolite monomethyl fumarate (MMF). Accordingly, the technology provided herein also contemplates the use of DMF and MMF in the treatment of sleep apnea. For example, in one embodiment, the FAE is in the form of the FAE metabolite dimethyl fumarate (DMF), which is also known as BG-12, BG00012, or FAG-201. BG-12 is an oral therapy studied in several clinical trials for the treatment of MS and is also in testing for treating rheumatoid arthritis.

Thus, FAE (e.g., FUMADERM) and DMF (e.g., BG-12) have found use as immunomodulatory agents to treat MS. See, e.g., Schimrigk, et al. 2006, "Oral fumaric acid esters for the treatment of active multiple sclerosis: an open-label, baseline-controlled pilot study" *Eur. J. Neurol.* 13: 604-610; Kappos L, et al. 2008, "Oral fumarate (BG00012) for relapsing-remitting multiple sclerosis: results of a phase 2b study" *Lancet* 372: 1463-1472; Lin, et al. 2011, "The anti-inflammatory effects of dimethyl fumarate in astrocytes involve glutathione and haem oxygenase-1", *ASN Neuro.* 3(2): e00055; Moharregh-Khiabani, et al. 2009, "Fumaric Acid and its Esters: An Emerging Treatment for Multiple Sclerosis", *Curr Neuropharmacol.* 7(1): 60-64.

In some embodiments, DMF (e.g., BG-12) is provided as a pharmaceutical composition sold under the trade name TECFIDERA (e.g., by Biogen Idec).

In some of these studies, FUMADERM or BG-12 was administered at doses ranging approximately from 100 to 1000 mg/d. Results of testing these compositions suggest that agents such as BG-12 have an immunomodulatory effect as well as a neuroprotective effect.

1.4. Other Immunotherapeutic Agents

In some embodiments other immunomotherapeutic agents, e.g., some associated with MS treatment, are contemplated as therapies for treating sleep apnea. For example, in some embodiments, compositions comprising natalizumab (an intravenous injectable anti-inflammatory monoclonal antibody used to treat MS and Crohn's disease), also known as TYSABRI, are used to treat sleep apnea.

In some embodiments, compositions comprising mitoxantrone (an anthrecenedione immunosuppressant and/or chemotherapeutic agent), also known as NOVANTRONE, are used to treat sleep apnea. These therapies are given intravenously.

In contrast, several orally administered drugs are also contemplated as therapies for sleep apnea, including cladribine, fingolimod, laquinimod, and teriflunomide.

Cladribine is a synthetic purine nucleoside analog and antineoplastic agent that has anti-inflammatory activity. See, e.g., Carson D A, et al. 1983, "Specific toxicity of 2-chlorodeoxyadenosine toward resting and proliferating human lymphocytes", *Blood.* 62: 737-743; Brousil J A, et al 2006, "Cladribine: an investigational immunomodulatory agent for multiple sclerosis" *Ann Pharmacother.* 40: 1814-1821. Cladribine has been effective as an injected and oral agent to treat MS. See, e.g., Dhib-Jalbut S. 1997, "Mechanisms of interferon beta action in multiple sclerosis", *Mult Scer.* 3: 397-401; Rieckmann P, et al. 2008, "Cladribine tablets in relapsing-remitting multiple sclerosis: study design of the 2-year, Phase IIIb CLARITY (CLAdRibine tablets Treating multiple sclerosis orallY) extension study", *Mult Scer.* 14: S161-S162; Montalban X, et al. 2007 "ONWARD Study Group Oral cladribine added to interferon beta-1a for active multiple sclerosis: a 96-week, double-blind, placebo-controlled phase IIb study", *Mult Scer.* 13 (Suppl 2): S245. Cladribine has been effective as an MS therapy when administered every 6 months.

Fingolimod, an oral immunosuppressant and sphingosine 1-phosphate receptor (S1PR) modulator that inhibits lymphocyte egress from lymph nodes, has been shown to be an effective treatment for MS in animal and human testing. See, e.g., Cohen J A, et al. 2010, "TRANSFORMS Study Group Oral fingolimod or intramuscular interferon for relapsing multiple sclerosis", *N Engl J Med.* 362: 402-415. Fingolimod is also known as GILENYA.

Laquinimod is a synthetic immunomodulatory derived from roquinimex. See, e.g., Brunmark C, et al. 2002 "The new orally active immunoregulator laquinimod (ABR-215062) effectively inhibits development and relapses of experimental autoimmune encephalomyelitis", *J Neuroimmunol.* 130:163-172. Laqinimod has been shown to be effective in treating MS in animal models, has been postulated to have neuroprotective activity in humans, and is effective in treating MS.

Teriflunomide is a reversible non-competitive inhibitor of dihydroorotate dehydrogenase that has immunomodulatory activity. Teriflunomide has been shown to be effective in human clinical trials as an MS treatment. See, e.g., Confavreux C, et al. 2010 "Safety of teriflunomide in the treatment of relapsing multiple sclerosis: results over an 8-year extension", *Mult Scer.* 16: S41-S196 (Abstract P8330); Li D K, et al. 2010 "Long-term brain MRI and clinical assessments of teriflunomide for the treatment of multiple sclerosis: extension of a phase II study", *Mult Scer.* 16: S41-S196 (Abstract P431); O'Connor P, et al. 2010 "A placebo-controlled phase III trial (TEMSO) of oral teriflunomide in relapsing multiple sclerosis: clinical efficacy and safety outcomes" *Mult Scier.* 16: S41-S196 (Abstract P79); Wolinsky J, O'Connor P, et al. 2010 "A placebo-controlled phase III trial (TEMSO) of oral teriflunomide in relapsing multiple sclerosis: magnetic resonance imaging (MRI) outcomes" *Mult Scer.* 16: S41-S196 (Abstract P982). Teriflunomide is also known as HMR1726 and A77 1726. Teriflunomide is sold by Sanofi under the trade name AUBAGIO.

Other agents that are contemplated to find use as agents to treat sleep apnea include alemtuzumab, PEGylated interferon beta-1a, daclizumab, ocrelizumab, rituximab, and Ethyl 2-[4-(12-beta-artemisininoxy)]phenoxylpropionate (SM933), which is a derivative of artemisinin (an herbal compound approved for the treatment of malaria) and has anti-inflammatory properties.

2. Pharmaceutical Formulations

In some embodiments, the technology relates to administration of a sleep apnea drug, e.g., an immunotherapeutic drug (e.g., such as beta-interferon or glatiramer acetate) to a subject in need of treatment for sleep apnea. In some embodiments, the technology comprises use of an immunotherapy that finds use in treating MS such as, e.g., beta-interferon or glatiramer acetate, and in some embodiments the technology comprises use of an immunotherapy that does not currently find use as a treatment for MS. The technology is intended and contemplated to embrace treating sleep apnea with immunotherapies and/or anti-inflammatory drugs. While drugs that currently find use in treating MS are typically administered by injection, it is contemplated that other dosage forms and routes of administration find use in the treatment of sleep apnea, for example, based on the chemical, physical, and biological characteristics (e.g., metabolism route, bioavailability, pharmacokinetics, etc.) of the particular immunotherapy.

It is generally contemplated that the immunotherapeutic compounds related to the technology are formulated for administration to a mammal, and especially to a human with a condition that is responsive to the administration of such compounds. Therefore, where contemplated compounds are administered in a pharmacological composition, it is contemplated that the contemplated compounds are formulated in admixture with a pharmaceutically acceptable carrier. For example, contemplated compounds can be administered orally as pharmacologically acceptable salts or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which, for example, may be easily accomplished with minor modifications (salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (e.g., acetylated or other) derivatives, pyridine esters, and various salt forms of the present compounds are preferred. One of ordinary skill in the art will recognize how to modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form and all metabolites of the compounds herein are therefore specifically contemplated. In addition, contemplated compounds (and combinations thereof) may be administered in combination with yet further agents for treating sleep apnea and related disorders, including, but not limited to hypertension, cardiovascular disease, coronary artery disease, insulin-resistance diabetes, depression, and sleepiness-related accidents.

With respect to administration to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication, and other factors that those skilled in the art will recognize.

Pharmaceutical compositions preferably comprise one or more compounds of the present technology associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro edit. 1985), explicitly incorporated herein by reference for all purposes.

Accordingly, in some embodiments, the immunotherapeutic agent is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of the immunotherapeutic agent over time.

In some embodiments, the compositions are formulated so that the active ingredient is embedded in a matrix of an insoluble substance (e.g., various acrylics, chitin) such that the dissolving drug finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustained-release formulations, the immunotherapeutic agent dissolves into the matrix and the matrix physically swells to form a gel, allowing the drug to exit through the gel's outer surface. In some embodiments, the formulations are in a micro-encapsulated form, e.g., which is used in some embodiments to produce a complex dissolution profile. For example, by coating the immunotherapeutic agent around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. "Particles" as used herein means nano- or microparticles (or in some instances larger) that can consist in whole or in part of the immunotherapeutic agent(s) as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, nonerodible, biodegradable, or nonbiodegradable material or combinations thereof. The particles may be microcapsules which contain the formulation in a solution or in a semi-solid state. The particles may be of any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylate), poly(ethyl methacrylate), poly(butyl methacrylate), poly (isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of the immunotherapy or salts thereof to inhibit formation of immunotherapy degradation products. A solution is provided that contains the immunotherapy or salts thereof and at least one immunotherapy inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the immunotherapy is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the immunotherapy is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof.

In some embodiments, the immunotherapy is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the immunotherapy is formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the immunotherapy is formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.30.9% W/V), parabens (0.01-5.0%), thimerosal (0.004-0.2%), benzyl alcohol (0.5-5%), phenol (0.1-1.0%), and the like.

In some embodiments, the immunotherapy is formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Immunotherapies have been administered subcutaneously and/or intramuscularly for treatment of MS. In some embodiments, subcutaneous and/or intramuscular administration may be used for the indications described herein. In other embodiments, different formulations and/or routes of administration (e.g., oral) are used.

3. Subjects

In some embodiments, the technology is related to administering an immunotherapy (e.g., an immunomodulatory agent) to a subject in need of a treatment for sleep apnea. In some embodiments, the subject is in need of treatment for sleep apnea and does not have MS; in some embodiments, the subject is in need of treatment for sleep apnea and has MS. In some embodiments, the subject is in need of treatment for sleep apnea and has not been nor is being treated for MS; in some embodiments, the subject is in need of treatment for sleep apnea and is being treated and/or has been treated for MS.

In some embodiments, the subjects have an apnea-hypopnea index (AHI) and/or a central apnea index (CAI) that is higher than a normal subject, e.g., one who does not have sleep apnea. For example, in some embodiments, a subject has an AHI of at least 5 apnea episodes per hour of sleep. In some embodiments, the subject has a significant component of central sleep apnea defined by a CAI of at least 5 episodes per hour of sleep (e.g., in the absence of severe obstructive sleep apnea). In some embodiments, the subject has a CAI that is at least 15 apnea episodes per hour of sleep in the presence of severe concomitant obstructive sleep apnea (e.g., an AHI greater than or equal to 30 episodes per hour of sleep). In addition, in some embodiments a patient is scored according to an accepted diagnostic definition of obstructive sleep apnea and/or central sleep apnea based on certain clinical criteria. For example, in some embodiments, the patient is scored according to the definitions and/diagnostic criteria for obstructive sleep apnea and/or central sleep apnea provided in a medical reference such as the International Classification of Sleep Disorders (ICSD), 2d Edition: Diagnostic and Coding Manual (American Academy of Sleep Medicine, 2005, incorporated herein by reference in its entirety for all purposes).

For example, according to the ICSD, the diagnostic criteria for a central sleep apnea include a patient reporting excessive daytime sleepiness, frequent arousals and awakenings during sleep or insomnia complaints, and/or awakening short of breath; and polysomnography showing five or more central apneas per hour of sleep. The diagnostic criteria for obstructive sleep apnea include a patient reporting unintentional sleep episodes during wakefulness, daytime sleepiness, unrefreshing sleep, fatigue, or insomnia; patient waking with breath holding, gasping, or choking; and/or the bed partner reporting loud snoring, breathing interruption, or both during the patient's sleep; and polysomnography showing five or more scoreable respiratory events (i.e., apneas, hypopneas, or respiratory event related arousals (RERAs)) per hour of sleep and evidence of respiratory effort during all or a portion of each respiratory event; or polysomnography showing fifteen or more scoreable respiratory events (i.e., apneas, hypopneas, or RERAs) per hour of sleep and evidence of respiratory effort during all or a portion of each respiratory event. One of skill in the art will recognize that the study of sleep disorders such as sleep apnea is ongoing and that definitions, such as the accepted diagnostic definitions of obstructive sleep apnea and/or central sleep apnea based on clinical criteria, e.g., as provided by the ICSD, may change from time to time.

In some embodiments, the subjects have a regional brainstem dysfunction, e.g., structural and ischemic brainstem syndrome. In some embodiments, the subjects have impaired respiratory control at the level of the medullary reticular formation. In some embodiments, the subject has dysarthria or dysphagia, lower cranial nerve dysfunction (e.g., diminished gag reflex, palatal asymmetry), and/or midbrain, pontine, or medullary lesions as detected by MRI (e.g., by T2-weighted or gadolinium-enhanced MRI). In some embodiments, the subjects have no known, readily demonstrable, and/or suspected neurological defect. Such is often the case, for example, in patents without MS who have obstructive sleep apnea or central sleep apnea.

In some embodiments, the subject has an elevated level of TNF-alpha and/or an elevated level of IL-6. In some embodiments, the subject has systemic or local inflammation.

4. Treatment

In some embodiments, an immunotherapy, a derivative thereof, or a pharmaceutically acceptable salt thereof, is administered in a pharmaceutically effective amount. In some embodiments, an immunotherapy, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of the immunotherapy or related compounds will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, the immunotherapy, a derivative thereof, or a pharmaceutically acceptable salt thereof, is administered orally.

In some embodiments, a single dose of an immunotherapy or a related compound is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years; for the subject's lifetime). In such embodiments, compounds may be taken on a regular scheduled basis (e.g., daily, weekly, etc.) for the duration of the extended period.

The technology also relates to methods of treating sleep apnea with an immunotherapy. According to another aspect of the technology, a method is provided for treating a subject in need of such treatment with an effective amount of an immunotherapy or a salt thereof. The method involves administering to the subject an effective amount of immunotherapy or salt thereof in any one of the pharmaceutical preparations described above, detailed herein, and/or set forth in the claims. The subject can be any subject in need of such treatment. In the foregoing description, the technology is in connection with an immunotherapy or salts thereof. Such salts include, but are not limited to, bromide salts, chloride salts, iodide salts, carbonate salts, and sulfate salts. It should be understood, however, that the immunotherapy (e.g., an immunotherapeutic agent) is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "immunotherapy" appears.

In some embodiments, a subject is tested to assess the presence, the absence, or the level of sleep apnea and/or a condition related to sleep apnea (e.g., hypertension, cardiovascular disease, coronary artery disease, insulin-resistance diabetes, depression, and sleepiness-related accidents). Such testing is performed, e.g., by assaying or measuring a biomarker, a metabolite, a physical symptom, an indication, etc., to determine the risk of or the presence of sleep apnea. In some embodiments, a quantitative score is determined, e.g., an AHI, a CAI, the number of apnea episodes per hour of sleep, etc. In some embodiments, testing for sleep apnea is related to testing for a condition such as hypertension, cardiovascular disease, coronary artery disease, insulin-resistance diabetes, depression, and sleepiness-related accidents. In some embodiments, the subject is treated with an immunotherapy based on the outcome of the test. Accordingly, in some embodiments, a subject is tested for sleep apnea and then treated for sleep apnea based on the test results. In some embodiments, a subject is treated for sleep apnea and then tested for sleep apnea to assess the efficacy of the treatment. In some embodiments, a subsequent sleep apnea treatment is adjusted based on a test result, e.g., the dosage amount, dosage schedule, identity of the drug, etc. is changed. In some embodiments, a patient is tested, treated, and then tested again to monitor the response to therapy and/or change the therapy. In some embodiments, cycles of testing and treatment may occur without limitation to the pattern of testing and treating (e.g., test/treat, treat/test, test/treat/test, treat/test/treat, test/treat/test/treat, test/treat/test/test, test/treat/test/test/treat/treat/treat/test, test/treat/treat/test/treat/treat, etc), the periodicity, or the duration of the interval between each testing and treatment phase.

In some embodiments, a patient with sleep apnea is treated first with other modalities, such as continuous or other forms of positive airway pressure, oral appliances, or surgery. An immunotherapeutic then offers a different or ancillary treatment. For example, a patient who cannot tolerate positive airway pressure or fails to be adherent to its nightly use may also refuse surgery and find that an oral appliance is ineffective; such a patient might then be given an immunotherapeutic agent(s) to treat sleep apnea.

EXAMPLES

During the development of the present technology, data were collected to assess the prevalence and severity of sleep apnea in (MS) patients referred for overnight polysomnography (PSG) and to explore radiographic and clinical features that might signal risk for undiagnosed sleep apnea. Apnea-hypopnea and central apnea indices (AHI and CAI) from laboratory-based PSG among 48 MS patients were compared to those of 84 sleep-laboratory-referred, non-MS patients matched for age, gender, and body mass index; and a separate group of 48 randomly selected, referred patients. Data collected demonstrate a predisposition for obstructive sleep apnea and accompanying central apneas among MS patients, particularly among those with brainstem involvement 1. Sleep-Disordered Breathing in Multiple Sclerosis
   1.1. Methods
   1.1.1. Standard Protocol Approvals, Registrations, and Patient Consents
   This retrospective data analysis was approved by the University of Michigan Institutional Review Board.
   1.1.2. Subjects/Data Collection
   Ms Cases:
   Demographic, clinical, and polysomnographic (PSG) data were assembled from medical records of 48 subjects, 18 years or older, who had an established diagnosis of MS and had completed a clinical overnight PSG between March 1999 and June 2010. Subjects with relevant PSG data were identified from the University of Michigan (U-M) Sleep Disorders Center database and from U-M MS Clinic lists. For subjects identified from MS clinic lists, patient registration numbers were used to search electronic charts for PSG reports using EMERSE, the Electronic Medical Record Search Engine. EMERSE is a web-based tool used to search for patient-specific information from the U-M Clinical Data Repository.
   Controls:
   Demographic, clinical, and PSG data from the U-M Sleep Disorders Center database were assembled for two separate control groups (Groups A and B). These groups were selected from more than 8,000 adult patients referred for diagnostic sleep studies. For the first group (Group A), two controls were matched to each MS patient for paired analyses, based on age (+/−5 years), gender, and body mass index (+/−2 $kg/m^2$). Matched controls were also selected based on date of study, pre- or post-Jan. 1, 2008, to control for minor changes in PSG scoring criteria that took place following Jan. 1, 2008 (see, e.g., Iber C. and American Academy of Sleep Medicine. *The AASM manual for the scoring of sleep and associated events: rules, terminology and technical specifications*. Westchester, Ill.: American Academy of Sleep Medicine; 2007, incorporated herein in its entirety for all purposes). Another sample of 48 control subjects (Group B) was selected using a random numbers table, for unpaired analyses that were not constrained a priori by matching criteria.

Polysomnography:

Full laboratory-based PSG and scoring followed existing standards before 2008 (see, e.g., Rechtshaffen A and Kales A. *A manual of standardized terminology, techniques and scoring system for sleep stages of human subjects*. Los Angeles: Brain Information Service/Brain Research Institute, UCLA; 1968, incorporated herein in its entirety for all purposes), and then slightly different, newly published standards from that point forward (Iber 2007, supra). The main relevant change concerned use of nasal pressure to identify hypopneas and rules employed to score them. Data collected for these studies had already quantified using thoracic or abdominal excursion changes, in addition to thermocouple airflow changes (when any of these were followed by awakenings, arousals, or ≥4% oxygen desaturations) to identify hypopneas in a sensitive manner before the AASM 2007 standards were published (see, e.g., Chervin R D and Aldrich M S. "Sleep onset REM periods during multiple sleep latency tests in patients evaluated for sleep apnea" *Am J Respir Grit Care Med* 2000: 161(2 Pt 1); 426-31). However, as the two approaches are not identical, care was taken to include in the MS and matched control Group A the same proportions of patients studied before and after the change in scoring rules.

The severity of sleep apnea is estimated by the number of episodes of apnea-hypopnea per hour of sleep. The metric is expressed using the apnea-hypopnea index (AHI), in which mild sleep apnea has a score of 5-15, moderate sleep apnea has a score of 15-30, and severe sleep apnea has a score of more than 30. In particular, an AHI score of more than 11 has been identified as an independent risk factor for cardiovascular disease (see, e.g., Shahar E, et al. 2001, "Sleep-disordered breathing and cardiovascular disease: cross-sectional results of the Sleep Heart Health Study" *Am J Respir Crit Care Med* 163:19-25).

The apnea-hypopnea index was calculated as the number of obstructive apneas, central apneas, or hypopneas per hour of sleep. The presence of obstructive sleep apnea was defined by an apnea-hypopnea index of at least 5 episodes per hour of sleep (see, e.g., "Sleep-related breathing disorders in adults: recommendations for syndrome definition and measurement techniques in clinical research", The Report of an American Academy of Sleep Medicine Task Force. *Sleep* 1999: 22(5); 667-89). Hypopneas are difficult to ascribe to obstructive or central etiologies, but they often make the major contribution to the apnea-hypopnea index. In addition, central apneas were included in the apnea-hypopnea index as generally practiced in sleep laboratories, in part because some degree of central sleep apnea is a common feature in obstructive sleep apnea. For this study, the separate presence of central sleep apnea or a significant component of central sleep apnea was defined by a central apnea index of at least 5 episodes per hour of sleep, in the absence of severe obstructive sleep apnea ("Sleep-related breathing disorders in adults: recommendations for syndrome definition and measurement techniques in clinical research", The Report of an American Academy of Sleep Medicine Task Force. *Sleep* 1999: 22(5); 667-89; "Central sleep apnea", *Med Clin North Am* 1985: 69(6); 1205-19). For individuals with severe obstructive sleep apnea (apnea-hypopnea index≥30 episodes per hour of sleep), we identified concomitant central sleep apnea by a central apnea index of 15 or more central apneas per hour of sleep.

Data Collection:

The following variables were extracted from the sleep database: gender, PSG date, age, body mass index (BMI), PSG diagnosis, apnea-hypopnea index (AHI, or rate of apneas and hypopneas per hour of sleep), and central apnea index (CAI). Data regarding total sleep time (TST) spent in the supine position, and the periodic leg movement index (PLMI) were also collected. Subjects who did not have BMI data recorded in either the sleep database or medical records (n=6) were excluded from paired analyses, but included in unpaired analyses. Individuals with concomitant diseases that could increase the risk of SDB, including severe cardiopulmonary disease, neurologic diseases other than MS or patients with coexistent non-MS brainstem neuropathology were excluded. For MS subjects, additional variables recorded included MS subtype (relapsing-remitting versus progressive), disease duration (years), use of disease modifying therapy (DMT, defined as glatiramer acetate or beta-interferon use at the time of PSG), estimates of disability (defined as an EDSS score of greater than or equal to 6.0), physical exam findings, and magnetic resonance imaging (MRI) results.

For subgroup analyses, MS patients with available MRI scans and/or physical exams were segregated by presence or absence of brainstem involvement, as suggested by the following: documented evidence of dysarthria or dysphagia; physical exam findings of lower cranial nerve dysfunction (diminished gag reflex, palatal asymmetry); or presence of T2 weighted or gadolinium-enhancing midbrain, pontine, or medullary MRI lesions. Faculty neuroradiologist-generated MRI reports from medical records were used to determine the presence of brainstem lesions. When reports did not specifically address the brainstem in the interpretation, the MRI studies were personally reviewed by an MS specialist to assess for the presence of T2 weighted signal changes or gadolinium enhancing lesions. These reviews were performed before any comparison to PSG data.

1.2. Statistical Methods

Statistical tests were performed using SAS version 9.2. Tests were two-sided with level of statistical significance set at 0.05.

Paired (Matched) Analyses:

Outcome variables AHI and CAI were compared between the MS subjects and matched controls (Group A). Comparisons were also made between MS subjects with brainstem involvement and their matched controls, and between MS subjects without brainstem involvement and their matched controls. The AHI comparisons were made using two-way ANOVA. Because of right skewness in AHI distribution, values were log-transformed (ln (x+1)) prior to performing two-way ANOVA. Due to persistent non-normality in the CAI distribution despite log-transformation, CAI comparisons were done using Wilcoxon Rank Sum tests. Differences in SDB prevalence were analyzed with Chi-square tests.

Unmatched Analyses:

Multiple linear regression models were used to identify significant predictors of AHI and CAI. To ensure residual normalization, CAI values were log-transformed prior to analysis. Raw AHI residuals were sufficiently normal for the regression models. Potential confounders taken into account in the regression model included BMI, age, and gender.

MS-Specific Unpaired Analyses:

We also conducted exploratory, post-hoc multiple linear regression analyses among MS subjects only, to assess whether MS subtype, duration, or treatment with DMT predicted AHI or log CAI, while adjusting for presence of brainstem lesions, age, gender, and BMI. As our sample size precluded use of a valid 7-variable model, we used the R-square selection method to select the 5 predictor variables that resulted in the highest R-square value for each model.

Forty-eight MS subjects with complete PSG data were identified. Mean disease duration was 13.1 years. No significant differences between MS subjects and matched (Group A) controls emerged for BMI, gender, or age. For those with available data, 1/28 (3.6%) of relapsing-remitting patients and 14/19 (73.7%) of progressive MS patients had an EDSS>=6.0. Twenty-one of twenty-nine (72.4%) of relapsing-remitting patients and 12/19 (63.2%) of progressive MS patients were on DMT. Among MS subjects, n=41 had MRI data available for unpaired analyses (24 cases with brainstem involvement and 17 cases without brainstem involvement). Among n=42 MS subjects with available BMI data for paired analyses, n=36 had MRI data available for matched subgroup analyses (20 cases with brainstem involvement and 16 cases without brainstem involvement).

Paired (Matched) Analyses:

Differences in mean AHI are summarized in Table 2.

TABLE 2

Mean apnea/hypopnea index (AHI) ± SD, log-transformed AHI, mean and median CAI are shown for multiple sclerosis (MS) patients; MS patients with brainstem lesions (+); MS patients without brainstem lesions (−); and their matched controls. AHI = apnea-hypopnea index; CAI = central apnea index

|  | Mean AHI ± SD | Log mean AHI ± SD | Two-way ANOVA p-value | Mean CAI ± SD | Median CAI (min-max) | Wilcoxon Rank-Sum p-value |
|---|---|---|---|---|---|---|
| MS cohort (n = 42) | 17.02 ± 18.76 | 2.48 ± 0.91 | 0.0011 | 3.47 ± 8.11 | 0.20 (0-42.0) | 0.0064 |
| Controls (n = 84) | 9.16 ± 8.84 | 1.95 ± 0.90 |  | 0.35 ± 1.13 | 0.0 (0-9.8) |  |
| Brainstem + (n = 20) | 21.28 ± 23.43 | 2.60 ± 1.09 | 0.0060 | 6.12 ± 11.11 | 0.3 (0-42.0) | 0.0215 |
| Controls (n = 40) | 8.67 ± 8.09 | 1.88 ± 0.94 |  | 0.14 ± 0.29 | 0.0 (0.0-1.6) |  |
| Brainstem − (n = 16) | 11.24 ± 8.13 | 2.35 ± 0.56 | 0.0091 | 0.99 ± 2.07 | 0.1 (0-7.8) | 0.4962 |
| Controls (n = 32) | 7.60 ± 7.05 | 1.86 ± 0.79 |  | 0.34 ± 0.61 | 0.0 (0.0-2.9) |  |

1.3. Results

Baseline Data:

Baseline characteristics for MS patients, matched (Group A) controls, and randomly selected (Group B) controls are shown in Table 1.

TABLE 1

Baseline characteristics of MS patients, matched controls (Group A), matched to n = 42 MS patients with available BMI data), and randomly selected controls (Group B) who had also been referred to the sleep laboratory.

| Variable | MS patients (n = 48) | Matched Controls Group A (n = 84) | Random Controls Group B (n = 48) |
|---|---|---|---|
| Age (years, mean ± SD) | 47.6 ± 10.8 | 46.9 ± 10.9 | 46.0 ± 10.2 |
| Female (n (%)) | 32 (67) | 31 (66) | 29 (61) |
| BMI (kg/m$^2$, mean ± SD) | 32.0 ± 5.2 | 31.9 ± 4.9 | 32.6 ± 5.7 |
| BMI >30 kg/m$^2$ (n (%)) | 24 (57.1) | 49 (58.3) | 31 (64.6) |
| Disease duration (years, mean ± SD) | 13.1 ± 10.4 | NA | NA |
| MS subtype |  |  |  |
| Relapsing-Remitting (n (%)) | 29 (60.4) | NA | NA |
| Secondary Progressive (n (%)) | 15 (31.2) |  |  |
| Primary Progressive (n (%)) | 4 (8.3) |  |  |

In comparison to 84 matched controls, the 42 MS subjects on average had a higher AHI (log-transformed, p=0.0011). Among MS subjects, 27 had obstructive sleep apnea, 2 had central sleep apnea, and 3 met diagnostic criteria for both. Total sleep time (TST) spent supine during sleep did not differ among MS patients and matched controls (165.2 and 197.8 minutes, respectively, two-way ANOVA p=0.1988).

Mean AHI among the 20 MS subjects with brainstem involvement was larger (in absolute value) than that of the entire MS cohort and remained higher than the mean AHI for these subjects' 40 matched controls (p=0.0060, Table 2 and FIG. 1). In contrast, absolute AHI differences between the 16 MS subjects without brainstem involvement and their 32 matched controls was less impressive.

Median CAI also differed between MS cases and controls (p=0.0064, Table 2). This difference increased when the analysis was focused on cases with brainstem involvement (p=0.0215, Table 2 and FIG. 1). In contrast, there was no difference between MS cases without brainstem involvement and their respective controls (p=0.4962).

Unmatched Analyses:

Table 3 shows differences between MS patients and randomly selected controls (group (b)) in mean AHI and log-transformed mean CAI values.

TABLE 3

Multiple linear regression results for three separate regression models in which all
MS patients, MS patients with brainstem involvement, or MS patients without brainstem
involvement, compared to Group B controls were modeled as predictors of AHI and log-
transformed CAI. Each model also accounted for age (years), BMI (kg/m$^2$), and gender.
Regression parameter = mean change in AHI (or log CAI) for 1-interval increase in
predictor variable; Model R$^2$ = the adjusted R-squared value that reflects the fraction
of the variation in mean AHI (or log CAI) explained by all covariates in the model.

|  | AHI | | | Log CAI | | |
|---|---|---|---|---|---|---|
|  | Regression parameter (SE) | p-value | Model R$^2$ (p-value) | Regression parameter (SE) | p-value | Model R$^2$ (p-value) |
| Entire MS cohort (n = 48) vs. Controls (n = 48) | | | | | | |
| Disease group | 7.34 (2.8) | 0.0118 | 0.21 (<0.0001) | 0.49 (0.16) | 0.0027 | 0.17 (0.0006) |
| Age | 0.49 (0.14) | 0.0006 | | 0.02 (0.01) | 0.0027 | |
| BMI | 0.49 (0.27) | 0.0791 | | 0.001 (0.02) | 0.9358 | |
| Male gender | 7.30 (3.13) | 0.0223 | | 0.10 (0.18) | 0.5619 | |
| Brainstem + MS Patients (n = 24) vs. Controls (n = 48) | | | | | | |
| Disease group | 11.87 (3.60) | 0.0016 | 0.28 (<0.0001) | 0.82 (0.19) | <0.0001 | 0.30 (<0.0001) |
| Age | 0.60 (0.16) | 0.0005 | | 0.03 (0.01) | 0.0004 | |
| BMI | 0.31 (0.31) | 0.3223 | | −0.01 (0.02) | 0.5113 | |
| Male gender | 6.74 (3.57) | 0.0639 | | 0.01 (0.19) | 0.9506 | |
| Brainstem − MS Patients (n = 17) vs. Controls (n = 48) | | | | | | |
| Disease group | 2.88 (2.50) | 0.2537 | 0.22 (0.0008) | 0.20 (0.14) | 0.1691 | 0.05 (0.1339) |
| Age | 0.32 (0.10) | 0.0022 | | 0.01 (0.01) | 0.2233 | |
| BMI | 0.54 (0.20) | 0.0087 | | −0.01 (0.01) | 0.3530 | |
| Male gender | 5.29 (2.31) | 0.0255 | | 0.15 (0.13) | 0.2692 | |

Consistent with the matched analyses, these unmatched analyses showed differences in AHI and log-CAI between the MS patients and controls, both before and after adjustment for BMI, age and gender (p=0.0118 and 0.0027, respectively). These differences increased in magnitude when the analysis focused on patients with brainstem involvement and controls, and diminished when the analysis was constrained to patients without brainstem involvement and controls.

MS-Specific Unpaired Analyses:

The presence of brainstem lesions, DMT use, disease subtype, age and gender were the best predictors of AHI (Table 4).

TABLE 4

Results for separate MS cohort regression analysis modeled using the R-square selection method.
Regression parameter = mean change in AHI (or log CAI) for 1-interval increase in
predictor variable; Model R$^2$ = the adjusted R-squared value that reflects the fraction
of the variation in mean AHI (or log CAI) explained by all covariates in the model.
MS patients only (n = 48)

| Best Predictor Variables for AHI | Univariable Analyses | | | Multivariable Analyses | | |
|---|---|---|---|---|---|---|
|  | Regression parameter (SE) | p-value | Model R$^2$ | Regression parameter (SE) | p-value | Model R$^2$ (p-value) |
| DMT | −12.92 (5.29) | 0.0184 | 0.0957 | −11.23 (5.47) | 0.0484 | 0.3795 (0.0057) |
| Brainstem lesions | 8.77 (5.78) | 0.1379 | 0.0331 | 6.04 (5.67) | 0.2941 | |
| Progressive MS | 15.52 (4.81) | 0.0023 | 0.1667 | 4.74 (7.42) | 0.5268 | |
| Age (years) | 0.63 (0.22) | 0.0082 | 0.1237 | 0.44 (0.33) | 0.1859 | |
| Male Gender | 7.67 (5.41) | 0.1632 | 0.0210 | 1.00 (5.90) | 0.8658 | |
| Best Predictor Variables for Log CAI | Regression parameter (SE) | p-value | Model R$^2$ (p-value) | Regression parameter (SE) | p-value | Model R$^2$ (p-value) |
| DMT | −0.85 (0.29) | 0.0048 | 0.1418 | −0.59 (0.33) | 0.0850 | 0.3665 (0.0022) |
| Brainstem lesions | 0.53 (0.34) | 0.1267 | 0.0366 | 0.38 (0.33) | 0.2637 | |

TABLE 4-continued

Results for separate MS cohort regression analysis modeled using the R-square selection method.
Regression parameter = mean change in AHI (or log CAI) for 1-interval increase in
predictor variable; Model R² = the adjusted R-squared value that reflects the fraction
of the variation in mean AHI (or log CAI) explained by all covariates in the model.
MS patients only (n = 48)

| Progressive MS | 0.78 (0.28) | 0.0068 | 0.1301 | 0.90 (0.45) | 0.0549 |
|---|---|---|---|---|---|
| Age (years) | 0.03 (0.01) | 0.0094 | 0.1190 | 0.02 (0.02) | 0.4087 |
| BMI (kg/m2) | 0.01 (0.03) | 0.7603 | −0.0226 | 0.03 (0.03) | 0.4212 |

Variables that best predicted log CAI included the presence of brainstem lesions, DMT use, disease subtype, disease duration and BMI.

There was no correlation between BMI and apnea indices (AHI and CAI, Pearson's rho=−0.0316 and 0.0224, p=0.8423 and 0.8882, respectively). The PLMI did not differ among subjects with or without brainstem involvement (6.8 and 16.0 respectively, 2-sample T-test p=0.1974).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method of treating a subject having sleep apnea, the method comprising administering dimethylfumarate to a subject having sleep apnea.

2. The method of claim 1 wherein the sleep apnea is obstructive sleep apnea or is central sleep apnea.

3. The method of claim 1 wherein the subject has:
   a) an apnea-hypopnea index of at least 5 apnea episodes per hour of sleep and/or recording;
   b) a central apnea index that is at least 5 episodes per hour of sleep in the absence of severe obstructive sleep apnea;
   c) an obstructive apnea index that is at least 5 episodes per hour of sleep;
   d) a central apnea index that is at least 15 episodes per hour of sleep in the presence of severe obstructive sleep apnea;
   e) an apnea-hypopnea index of greater than or equal to 30 episodes per hour of sleep;
   f) a diagnosis of obstructive sleep apnea or central sleep apnea determined by an index or measure from a sleep laboratory or home sleep study;
   g) a diagnosis of obstructive sleep apnea or central sleep apnea determined by physical exam finding or symptoms of sleep apnea; or
   h) increased expression of tumor necrosis factor-alpha (TNF alpha) or interleukin-6 (IL-6) relative to expression of TNF alpha or IL-6 in a normal subject.

4. The method of claim 1 wherein the dimethylfumarate is administered as a pharmaceutical formulation.

5. The method of claim 1 further comprising testing the subject for sleep apnea.

6. The method of claim 1 wherein the administering improves sleep quality or sleep quantity of the subject; reduces or eliminates one or more symptoms of sleep apnea; prevents increased severity of one or more symptoms of sleep apnea; or reduces, prevents, or eliminates a sleep apnea-related condition selected from the group consisting of hypertension, cardiovascular disease, coronary artery disease, insulin-resistance diabetes, depression, and sleepiness-related accident.

7. The method of claim 1 comprising co-administering an additional therapeutic agent or an additional medical intervention.

8. The method of claim 7 wherein the medical intervention is continuous positive airway pressure (CPAP), surgery, or weight loss.

9. The method of claim 1 wherein the subject does not have multiple sclerosis and/or wherein the subject is not in need of a treatment for multiple sclerosis and/or wherein the subject has not been treated for multiple sclerosis.

10. The method of claim 5 further comprising a second testing after the administering.

11. The method of claim 5 further comprising a second administering after the testing.

12. The method of claim 10 wherein the testing produces a first quantitative sleep apnea score and the second testing produces a second quantitative sleep apnea score and a relative change in the second quantitative sleep apnea score compared to the first quantitative sleep apnea score indicates an amelioration of sleep apnea in the patient.

13. The method of claim 11 wherein the testing produces a quantitative sleep apnea score that is used to change the dosage amount or dosage schedule of the second administering relative to the administering.

14. The method of claim 12 wherein:
   a) the quantitative sleep apnea score is determined using the Apnea-Hypopnea Index (AHI);
   b) the quantitative sleep apnea score is determined using the Central Apnea Index (CAI);
   c) the quantitative sleep apnea score is determined by polysomnography; and/or
   d) the quantitative sleep apnea score is determined by a home sleep apnea test.

15. The method of claim 13 wherein:
   a) the quantitative sleep apnea score is determined by AHI;
   b) the quantitative sleep apnea score is determined by CAI; and/or
   c) the quantitative sleep apnea score is determined by polysomnography; and/or
   d) the quantitative sleep apnea score is determined by a home sleep apnea test.

* * * * *